United States Patent [19] [11] 4,358,679
Lipoma [45] Nov. 9, 1982

[54] CALIBRATION OF ANALYZERS EMPLOYING RADIANT ENERGY

[75] Inventor: Phillip C. Lipoma, Dickinson, Tex.

[73] Assignee: Astro Safety Products Inc., League City, Tex.

[21] Appl. No.: 183,460

[22] Filed: Sep. 2, 1980

[51] Int. Cl.³ .......................... G01D 18/00; G01J 1/00
[52] U.S. Cl. ................................ 250/252.1; 250/343
[58] Field of Search ............... 250/338, 343, 351, 352, 250/353, 252; 356/51, 437

[56] References Cited

U.S. PATENT DOCUMENTS

| | | |
|---|---|---|
| 2,775,160 | 12/1956 | Foskett et al. |
| 2,834,246 | 5/1958 | Foskett et al. |
| 3,560,736 | 2/1971 | Billetdeaux et al. ................. 250/343 |
| 4,013,260 | 3/1977 | McClatchie et al. ................ 250/343 |
| 4,233,513 | 11/1980 | Elder et al. .......................... 250/352 |

Primary Examiner—Alfred E. Smith
Assistant Examiner—Janice A. Howell
Attorney, Agent, or Firm—Russell H. Schlattman

[57] ABSTRACT

A method and apparatus for checking the calibration of analyzers employing radiant energy is disclosed. The invention embodies changing the radiant energy source color temperature by a precise increment and adjusting the span to reflect the predetermined amount of differential absorbance between reference and analytical interference filters which would result from said increment of change in source color temperature. The invention is particularly useful when employing radiant energy in the ultraviolet, visible and infrared spectra. The invention eliminates the need for standard liquid or gaseous calibration solutions or special optical calibration filters.

10 Claims, 2 Drawing Figures

CALIBRATION OF ANALYZERS EMPLOYING RADIANT ENERGY

BRIEF SUMMARY OF THE INVENTION

This invention relates generally to a novel method and apparatus for checking the calibration of analytical instruments of the type wherein the determination of the desired constituent content of gases and liquids is based upon the ability of the desired constituent to absorb radiant energy at specific wavelengths. The invention is particularly useful in devices employing sources emitting energy in the ultraviolet, visible spectrum and infrared wavelengths. The invention will be more particularly described herein in connection with its utility in infrared analysis notwithstanding its equal applicability in analysis employing ultraviolet or visible spectrum energy. Specifically stated, this invention concerns the novel use of discretely changing a radiant energy source color temperature, for example an infrared source color temperature, by a pre-determined amount to simulate differential absorbance normally related to a specific gas or liquid concentration.

BACKGROUND OF THE INVENTION

Controlling the temperature of a blackbody radiator allows the generation of a determinable amount of infrared energy at known wavelengths. Certain species of gases and liquids absorb a determined amount of infrared energy at unique wavelengths as a function of path length and concentration. Detection of this absorbance has been successfully used to determine concentration values of the species of interest. Infrared analyzers precisely and accurately control the source temperature with current and voltage regulation devices. Great caution in design is exercised to assure the source temperature is constant in all modes of operation and calibration. The prior art devices require interrupting on-line process measurements to perform time-consuming and costly calibration and operational checks, to the detriment of production efficiency. In critical operations, the use of redundant infrared analyzers minimize process down-time but at the expense of added cost and complexity. A more reliable method and apparatus that does not require lengthy and costly interruptions for calibration and operational checks are needed.

Infrared analysis of a wide range of gases and liquids is a well-known art, relying on the physical phenomenon that many species absorb infrared energy at specific wavelengths. For example, carbon dioxide ($CO_2$) absorbs infrared energy at about 4.25 microns; carbon monoxide (CO) absorbs infrared energy at about 4.63 microns. The amount of infrared energy absorbed by the species is a direct function of the gas or liquid concentration and path length of the species at its unique wavelength.

In the past, there have been only two reported methods of checking the calibration of infrared analyzers. The first, and most common method, is to introduce a known gas or liquid standard solution into the measuring cell of the infrared analyzer. The decrease in infrared energy measured at the infrared detector at the specific wavelength in question allows the instrument to be properly spanned related to concentration values. In order to check the calibration of an operating infrared analyzer, general practice is to by-pass the stream sampled and divert standard solutions of gases or liquids to the infrared analyzer measuring cells through suitable valves, either manually or electrically controlled, and ascertain that correct calibration values are achieved.

The second method is to insert a calibrating filter into the measuring path between the infrared light source and the infrared detector. The calibrating filter is manufactured to produce a defined absorbance of the infrared energy at the wavelength of interest, thus affording the condition to properly span the infrared analyzer to the simulated gas or liquid concentration desired or to check the calibration or operation of the analyzer by momentarily inserting the filter.

The first method is cumbersome, expensive and the handling of gas cylinders is usually hazardous.

The second method requires solenoids, motors or other mechanical devices which are cumbersome, expensive, use significant amounts of power and after long periods of un-attendance and/or the neglect of lubrication, they become gummy, sticky and generally inoperative.

The problems of cost and complexity enumerated in the foregoing with respect to the above prior art systems are not intended to be exhaustive, but rather are among many which tend to impair the effectiveness of previously known devices and methods for checking the calibration of infrared analyzers operating on liquid or gas process streams. Other noteworthy problems may exist. However, those presented above should be sufficient to demonstrate that devices and methods for checking the calibration of infrared analyzers appearing in the prior art have not been altogether satisfactory.

It is an object of this invention to provide an improved method and apparatus for checking the calibration of analyzers herein described.

It is a particular object of this invention to provide an improved method and apparatus for checking the calibration of infrared analyzers for determining specific constituent content of gases and liquids.

Other objects will become apparent from the description of the invention as set forth herein.

DETAILED DISCUSSION OF THE INVENTION

Specifically stated, this invention covers the method of calibrating an analyzer employing differential absorbance of radiant energy between an analytical interference filter and a reference interference filter as a measure of a specific constituent content of a gas or liquid, which comprises changing the source color temperature by a precise increment and adjusting the gain or span to reflect the predetermined amount of differential absorbance which would result from said increment of change in source color temperature.

This invention also covers an improved apparatus for carrying out analysis of gases and liquids, said apparatus having in combination a sample cell, a radiant energy source, an analytical interference filter, a reference interference filter, means for passing a beam of energy from said energy source alternately through each of said filters and the sample to be analyzed in said sample cell, means for measuring the differential absorbance between said filters and means for converting said differential absorbance into a useable output signal, the improvement which comprises means for changing the source color temperature by a precise increment and means for adjusting said output signal to indicate the predetermined differential absorbance to be realized by said change in source color temperature, thereby calibrating the instrument.

Figure 1:
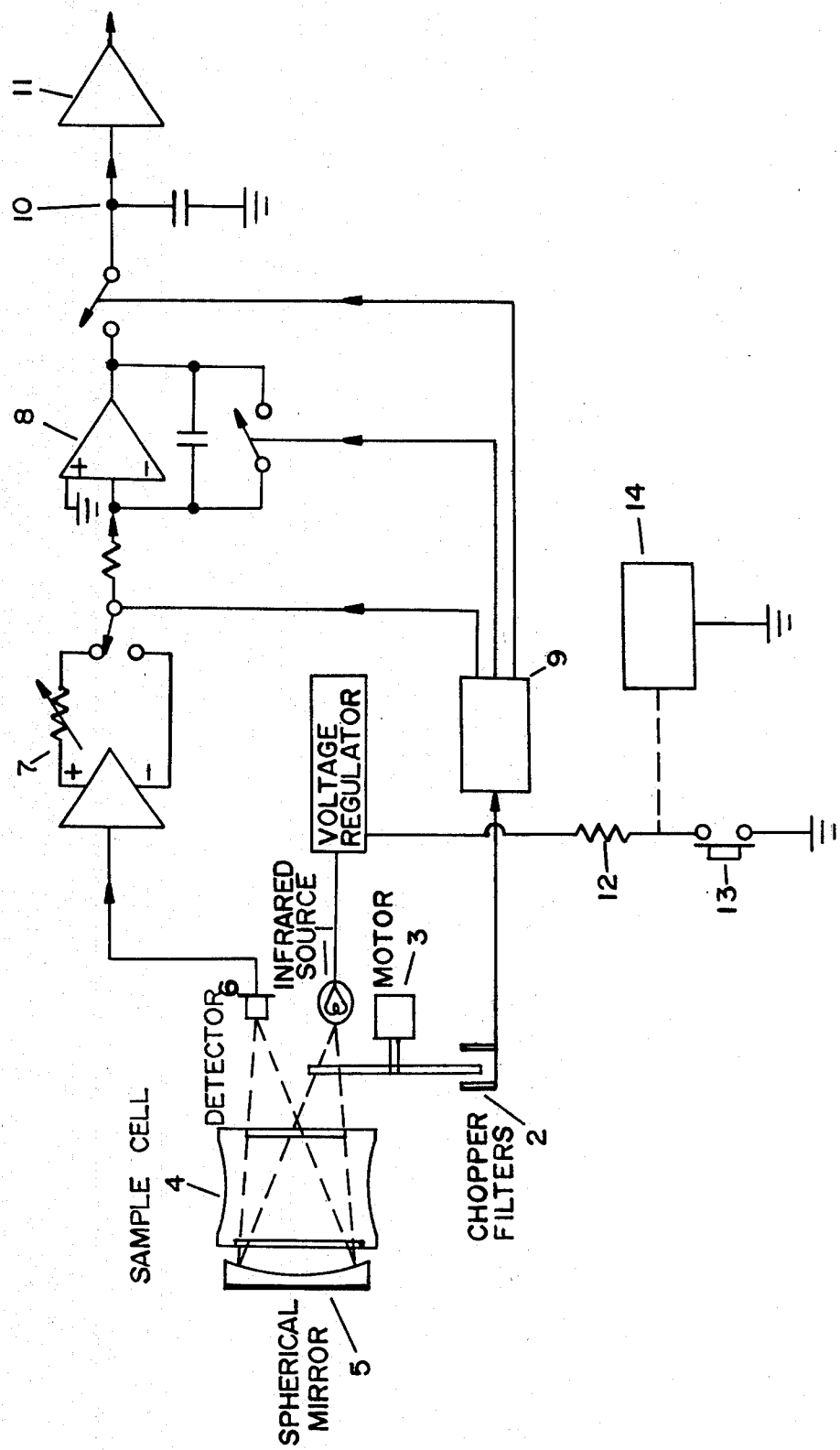
FIG. 1 is a block diagram of an infrared analyzer and device depicting an embodiment of the present invention.

A specific preferred embodiment of this invention is illustrated as follows:

FIG. 1 depicts in block diagram form infrared analyzers embodying the improvement of this invention. In its operation, infrared energy from source (1), passes through chopper/interference filters (2), which are oscillated by motor (3), through the sample cell (4), where it is reflected by spherical mirror (5), returned back through the sample cell (4), impinging on detector (6). The resulting signal is amplified by pre-amplifier (7), differentially detected by electronic integrator (8), and timing signals (9), the difference stored by sample and hold circuitry (10), and provided at the output by buffer (11). To check calibration of the instrument, power change means (resistance) (12), is provided to provide a precise incremental change in power to infrared energy source (1), either manually (13), or by means of an auto timer (14).

Figure 2:
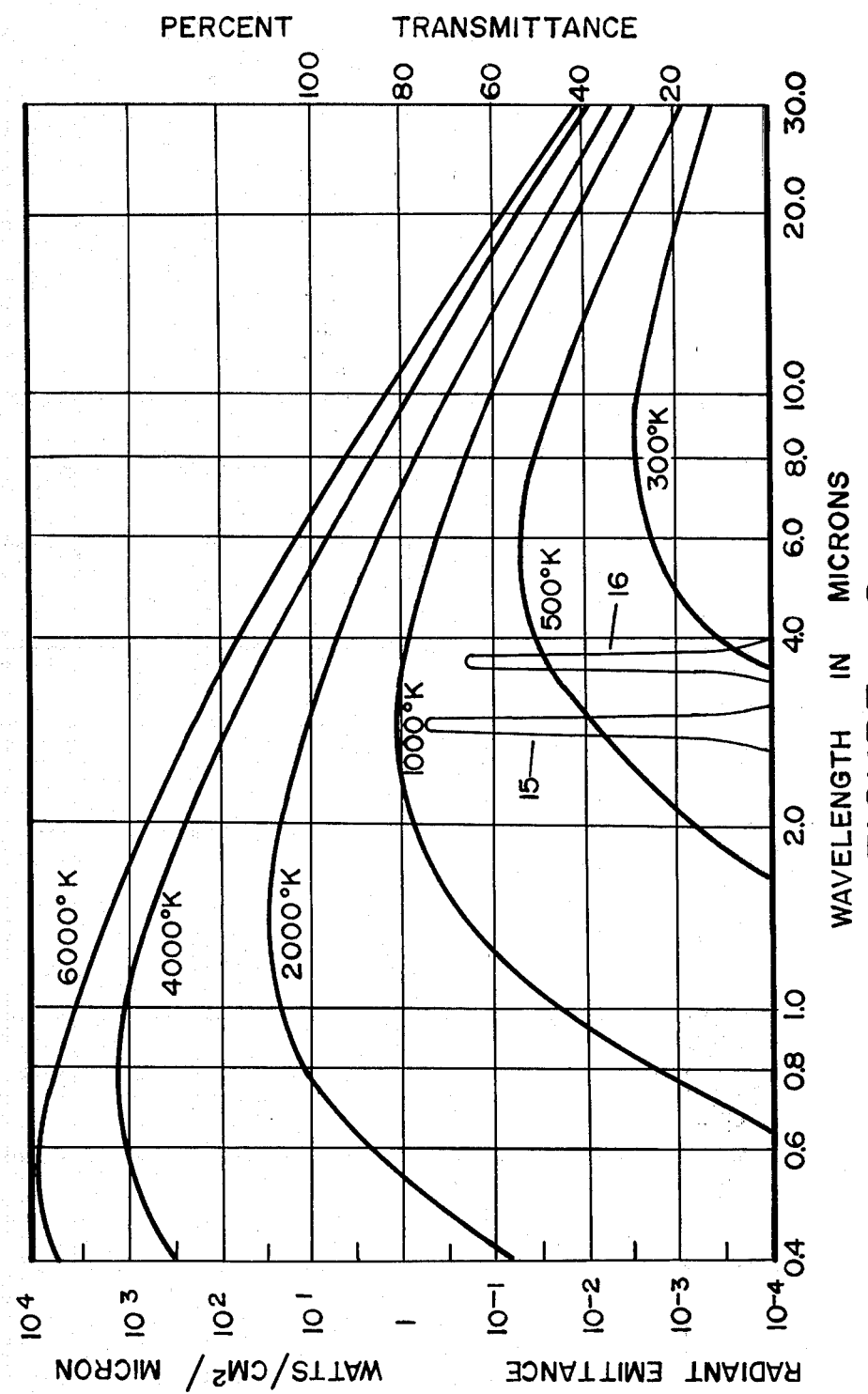
FIG. 2 is a chart of the Spectral Radiant Emmittance of Black Bodies at various temperatures with a superposition of spectral characteristics of two species of interest as examples of an embodiment of the present invention.

To illustrate a specific application, the above described analyzer can be used to determine the amount of certain combustible hydrocarbons in air for various purposes, such as warning of approaching explosive conditions. In such an instrument, the sample cell was a cylinder approximately 7.5 cm. in length and 3 cm. in diameter. Sufficient opening was provided along its length such that the sample enveloped within the cylinder was constantly representative of current atmospheric conditions. The analytical interference filter (15), used transmitted infrared energy at a wavelength of approximately 3.3 microns and the reference interference filter (16), transmitted infrared energy at a wavelength of approximately 3.8 microns, as shown in FIG. 2. The instrument employed a primary source power of approximately 2.5 watts and means for altering the source power by 0.3 watts for checking calibration. In this instance, a reduction of source power by 0.3 watts resulted in a 14% up scale output change. Periodic checking of the calibration of this instrument is accomplished by merely reducing the power supply by 0.3 watts and, if necessary, adjusting the instrument to reflect the 14% up scale output change.

While the apparatus and method of this invention is applicable to analyzers employing radiant energy broadly, it is particularly applicable to analyzers employing radiant energy in the ultraviolet spectrum, visible spectrum and infrared spectrum. A preferred embodiment of this invention employs radiant energy in the infrared spectrum having wavelengths of less than about 15 microns.

It will be obvious to those skilled in the art that the operation and output signal of analyzers utilizing the improvement of this invention can be modified in many ways using techniques, devices and circuitry well known in the art. Such examples include the use of the output signal to give a direct reading of the analytical result, provided a continuous recording of the analytical result, activate an alarm system when a predetermined analytical result is reached, etc.

It will also be obvious to those skilled in the art that the calibration check provided by the improvements of this invention can be accomplished in several ways without departing from the scope of this invention. In addition to providing the means for manual calibration at any desired time, the calibration check can be fully automated. Using well known techniques, the instrument can be made to automatically check calibration at predetermined intervals, sound an alarm if the calibration check indicates an out-of-tolerance condition with respect to predetermined values stored in an electronic memory device or automatically correct out-of-tolerance conditions and recalibrate the instrument accordingly.

Analyzers employing the improvement of this invention can be used to analyze for the content of specific constituents of gases and liquids, wherein the specific constituents absorb radiant energy at specific known wavelengths. Since the method of checking the calibration of analyzers as covered by this invention can be carried out without removing or changing the sample in the sample cell being analyzed, considerable savings in down-time for calibration is obviously realized.

What is claimed is:

1. The method of calibrating an analyzer in which differential absorbance of radiant energy between an analytical interference filter and a reference interference filter is converted into an output signal useable as a measure of a specific constituent content of a gas or liquid being analyzed, which comprises changing the radiant energy source color temperature by a precise increment which, when the analyzer is in calibration, will cause the output signal to indicate a known amount of change in the differential absorbance and adjusting the analyzer to indicate said known amount of change in the differential absorbance.

2. The method of claim 1 wherein the radiant energy employed in the analyzer is in the ultraviolet spectrum.

3. The method of claim 1 wherein the radiant energy employed in the analyzer is in the visible spectrum.

4. The method of claim 1 wherein the radiant energy employed in the analyzer is in the infrared spectrum.

5. The method of claim 1 wherein the radiant energy employed in the analyzer is infrared energy having a wavelength of less than about 15 microns.

6. In an apparatus for carrying out analysis of gases and liquids, said apparatus having in combination a sample cell, a radiant energy source, an analytical interference filter, a reference interference filter, means for passing a beam of energy from said energy source alternately through each of said filters and the sample to be analyzed in said sample cell, means for measuring the differential absorbance between said filters and means for converting said differential absorbance into a useable output signal, the improvement which comprises means for changing the energy source color temperature by a precise increment and means for adjusting said measurement means to indicate the predetermined differential absorbance to be realized by said change in source color temperature.

7. An apparatus as described in claim 6 wherein the radiant energy source is a source of energy in the ultraviolet spectrum.

8. An apparatus as described in claim 6 wherein the radiant energy source is a source of energy in the visible spectrum.

9. An apparatus as described in claim 6 wherein the radiant energy source is a source of energy in the infrared spectrum.

10. An apparatus as described in claim 6 wherein the radiant energy source is a source of energy in the infrared spectrum having a wavelength less than about 15 microns.

* * * * *